United States Patent [19]

Kharitonov et al.

[11] Patent Number: 5,110,995
[45] Date of Patent: May 5, 1992

[54] PREPARATION OF PHENOL OR PHENOL DERIVATIVES

[75] Inventors: Alexandr S. Kharitonov; Gennadii I. Panov; Kazimira G. Ione; Vyacheslav N. Romannikov; Galina A. Sheveleva; Lidia A. Vostrikova; Vladimir I. Sobolev, all of Novosibirsk, U.S.S.R.

[73] Assignee: Institute of Catalysis, Novosibirsk, U.S.S.R.

[21] Appl. No.: 668,085

[22] Filed: Mar. 12, 1991

[51] Int. Cl.⁵ ............ C07C 37/60; C07C 46/06; C07C 50/04; C07C 39/26
[52] U.S. Cl. .................... 568/800; 552/293; 568/741; 568/771
[58] Field of Search ............ 568/800, 767, 771, 741; 552/293

[56] References Cited

U.S. PATENT DOCUMENTS

| | | | |
|---|---|---|---|
| 4,478,752 | 10/1984 | Hsu et al. | 552/293 |
| 4,522,757 | 7/1985 | Hsu et al. | 552/293 |
| 4,973,720 | 11/1990 | Saito et al. | 552/293 |
| 5,055,623 | 10/1991 | Gubelmann et al. | 568/800 |

FOREIGN PATENT DOCUMENTS

| | | | |
|---|---|---|---|
| 0341165 | 11/1989 | European Pat. Off. | 568/800 |
| 0184036 | 9/1985 | Japan | 568/800 |
| 1236738 | 10/1986 | Japan | 568/800 |
| 0535282 | 11/1976 | U.S.S.R. | 532/282 |

*Primary Examiner*—Werren B. Lone
*Attorney, Agent, or Firm*—William C. Long

[57] ABSTRACT

The invention relates to a process for the production of phenol or phenol derivatives by oxidation of the aromatic nucleus of benzene or benzene derivatives with nitrous oxide over a zeolite catalyst.

11 Claims, No Drawings

PREPARATION OF PHENOL OR PHENOL DERIVATIVES

BACKGROUND OF THE INVENTION

1. Field of the Invention

The present invention relates to organic synthesis and, more particularly, to processes for preparing phenol or derivatives.

2. Description of the Prior Art

Oxygen-containing benzene derivatives such as phenol, dihydric phenols, benzoquinone, chlorophenols, cresols, ethylphenols, nitrophenols and the like are valuable products and find an extensive use for various applications. The most mass-scale prepared product of this class is phenol, the basic amount of which is intended for the production of phenolic resins, synthesis of adipic acid, caprolactam, bisphenol, nitro- and chlorophenols, phenol sulphonic acids and the like. Dihydric phenols are employed in photography, as well as antioxidants and modifying agents for stabilization plastics. Cresols are used for the production of cresol-formaldehyde resins; chlorophenols for the manufacture of herbicides; benzoquinone as a raw material for the preparation of hydroquinone and the like.

Known in the art is a principal possibility for preparing oxygen-containing benzene derivatives by way of a direct oxidation of benzene and derivatives thereof. However, all the attempts to carry out these reactions with an acceptable selectivity repeatedly undertaken during recent decades has proved to be unsuccessful. For example, the main products of oxidation of benzene with molecular oxygen, depending on conditions, are either maleic anhydride (on specially selected catalysts) or products of a complete oxidation, whereas phenol and benzoquinone are formed but in trace amounts. In a direct oxidation of benzene derivatives, such as toluene, the oxidation process affects the functional group in the first place with the formation of benzaldehyde and benzoic acid, but the formation of cresols is not observed (G. I. Golodetz. Heterogeneous-Catalytic Oxidation of Organic Compounds. Kiev, "Naukova Dumka" Publishing House, 1978, pp. 209–224).

There are a number of processes for the production of oxygen-containing benzene derivatives (L. Tedder, A. Nechvatal, A. Jubb. Industrial Organic Chemistry, Moscow, "MIR" Publishers 1977, pp. 198–205). In the preparation of phenol, the most widely used is the so-called cumene process accounting for more than 90% of the world output of phenol (J. Econ. and Eng. Review, 1982, vol. 14, No. 5, p. 47). This process consists of three stages:

alkylation of benzene with propylene to give cumene (isopropylbenzene);

oxidation of cumene to cumene hydroperoxide;

decomposition of cumene hydroperoxide with the formation of phenol and equimolar amounts of acetone.

This is a multi-stage process, and its efficiency depends to a great extent on the possibility for commercialization of acetone. However, recently there has been a declining trend in the demand for acetone which in the foreseeable future may result in the necessity of abandoning the cumene process (Kohn P. M., Bolton L., Cottrell R., McQueen S., Ushio S., Chem. Eng. (USA), 1979, vol. 86, No. 8, pp. 62–64).

Known in the art is a process for preparing phenol (Iwamoto M. Hirata J., Matsukami K., Kagawa S., J. Phys. Chem., 1983, vol. 87, No. 6, pp. 903–905) by way of oxidation of benzene with nitrous oxide at a temperature of 550° C.–600° C.:

$$C_6H_6 + N_2O = C_6H_5OH + N_2$$

In this case as the catalyst use is made of vanadium oxide, molybdenum oxide and tungsten oxide. To improve selectivity water vapors are added to the reaction mixture. The best results were obtained on a catalyst 3.3% $V_2O_5/SiO_2$ at the temperature of 550° C. at the following composition of the reaction mixture: 8.2% benzene, 16.9% nitrogen oxide and 30.7% water. Conversion of benzene under these conditions, X, was 10.7%, selectivity, S, gas 71.5% which corresponded to a yield, Y, of phenol of 7.7% (Y=X.S).

However, this process features an insufficient yield of phenol; the process requires a high temperature and introduction of water into the reaction mixture which necessitates additional power consumption for its evaporation and complicates isolation of the desired product. This process was not practiced on a commercial scale. This was apparently associated with an insufficient selectivity as well. The selectivity parameter is of a great importance for this reaction, since lowering of selectivity due to over oxidation means not only an increased benzene consumption, but especially high consumption of nitrous oxide.

To prepare more complex oxygen-containing benzene derivatives, two possibilities can be used. The first envisages introduction of a required functional group into the respective oxygen-containing benzene derivative; the second resides in a direct oxidation of the respective benzene derivative. The difficulties of carrying out the less complicated reaction of preparation of phenol from benzene would be also encountered in the production of other oxygen-containing benzene derivatives. But in this case, the problem of selectiveness is still more acute and, hence, that of the process efficiency, since the number of possible directions of the reaction (o-, p- and m-isomers, participation of functional groups in the chemical transformation) considerably increases.

For example, the process for preparing dihydric phenols is known which is effected in a manner similar to that of the cumene process for the preparation of phenol and which features a multi-stage character and the necessity of commercialization of acetone formed in large quantities (Vorozhtsov N. N. Foundations fo Synthesis of Intermediate Products and Dyestuffs. M., Goskhimizdat Publishers, 1955, p. 621). In this process, alkylation of benzene with propylene is effected in the first stage with propylene; in so doing, there is possible the formation of three isomers of diisopropyl and triisopropylbenzene. Then, the corresponding derivatives of diisopropylbenzene are oxidized into cumene hydroperoxides and, finally, decomposition of cumene dihydroperoxide is effected in the last stage of the process.

There is a number of processes for the preparation of dihydric phenols, as well as chlorophenols and phenolsulphonic acids based on an alkali treatment of corresponding chloro- and sulpho-benzene derivatives. These processes, however, necessitate the use of aggressive reagents—concentrated acids and alkalis and are accompanied by the formation of several tons of alkaline and acidic effluents per ton of the product, thus complicating the problem of the environment pollution.

Known in the art is another process for the preparation of oxygen-containing benzene derivatives, in particular phenol and chlorophenol (Suzuki E., Nakashiro K., Onoy Y., Chemistry Letters, 1988, No. 6, pp. 953-956). In this process, benzene or chlorobenzene in the vapor phase are subjected to oxidation with nitrous oxide on a pentasil-type catalyst of an alumosilicate composition with the ratio of $SiO_2/Al_2O_3 = 85$ at the temperature of 330° C. with the following composition of the reaction mixture: 6.9 mol. % benzene, 51 mol. % nitrous oxide, nitrogen being the balance. The time of contact of the gas mixture with the catalyst is 2 seconds. The yield of phenol in this case is 5.5%. Under similar conditions (temperature 330° C., 3.9% chlorobenzene, 71% nitrous oxide, the contact time—2 seconds) in the oxidation of chlorobenzene, yields of chlorophenol did not exceed 6.7%. The use of an alumosilicate catalyst as compared to the above-mentioned vanadium catalyst (Iwamoto M., Hirata J., Matsukami K., Kagawa S., J. Phys. Chem. 1983, vol. 87, No. 6, pp. 903-905) made it possible to substantially simplify the process by carrying out the same without introduction of water vapors into the reaction mixture. However, yields of phenol and chlorophenol in this process remained low, 5.5% and 6.7% respectively.

Known in the art is another process for phenol preparation (Gubelmann, et al. EP 341,165 and U.S. Pat. No. 5,001,280) by way of benzene oxidation with nitrous oxide. Like Suzuki, et al., Gubelmann, et al. make use of zeolite catalysts of aluminosilicate composition but of a greater $SiO_2/Al_2O_3$ ratio ranging from 90 to 500. Higher phenol yields up to 16% at 400° C. are shown but, nevertheless, such yields are not sufficiently high.

It is an object of the present invention to provide such a process for preparing oxygen-containing benzene derivatives which would make it possible to obtain the desired products in a sufficiently high yield following a simple procedure.

SUMMARY OF THE INVENTION

This object is accomplished by the process for preparing phenol or derivatives by way of oxidation of aromatic nucleus of benzene or derivative thereof with nitrous oxide at an elevated temperature in the presence of a zeolite catalyst.

DETAILED DESCRIPTION

According to the present invention, the oxidation of benzene or derivatives thereof is effected at a temperature within the range of 275° C. to 450° C., a time of contact of the reaction mixture with the catalyst of not more than 8 seconds and using, as the catalyst, a zeolite of the composition $y.El_2O_n.x.Fe_2O_3.SiO_2$, wherein $y = 0-6.5 \cdot 10^{-2}$, $x = 1.5 \cdot 10^{-5} - 2 \cdot 10^{-2}$, El at least one of elements of 2, 3, 4, 5 Periods of the periodic system; n is valence of the element.

At $y = 0$ the catalyst has an iron-silicate composition $x.Fe_2O_3.SiO_2$. The use of iron-silicates as catalysts of partial oxidation is unknown in the literature and is not obvious, since none of the components of the principal composition ($Fe_2O_3$, $SiO_2$) is a catalyst of reactions of this type.

The incorporation, into the catalyst, of elements of Periods 2, 3, 4 and 5 of the periodic system changes its properties. Thus, zeolites incorporating aluminum are more active, all other conditions being equal. With an increasing content of sodium, the catalyst activity is lowered. If an iron silicate additionally incorporates more than one element, "y" is the total of molar coefficients of corresponding oxides of the elements introduced additionally into the zeolite. For example, if the catalysts composition corresponds to the formula:

$1.1 \cdot 10^{-2}.CaO.4.2 \cdot 10^{-3}MgO.10^{-2}.Al_2O_3.3.4 \cdot 10^{-3}.Fe_2O_3.SiO_2$, than "y" $= 1.1 \cdot 10^{-2} + 4.2 \cdot 10^{-3} + 10^{-2} = 2.52 \cdot 10^{-2}$ and the sum of molar coefficient cannot exceed $6.5 \cdot 10^{-2}$.

As the catalysts use is made of high-silica zeolites of various structural types: pentasils (ZSM-5, ZSM-11, ZSM-12, ZSM-23), mordenites, BETA, EU-1.

Only the use of zeolite catalysts of the above-mentioned composition and of a process temperature within the range of 275° C. to 450° C. makes it possible to accomplish the object of the present invention: to increase the yield of the desired product, e.g. phenol, up to 38%.

It is a strictly observed optimal composition of the catalyst that ensures its catalytic properties. A lowered or an increased content of corresponding components beyond the limits of the above-specified range results in a reduced yield of the desired product either due to a decreased conversion of benzene or a derivative thereof, or due to an impaired selectivity of the process. For the same reason, it is inexpedient to use an elevated or a lowered temperature. The change of the molar ratio $C_{C_6H_6}/C_{N_2O}$ does not substantially affect yields of the desired product; with an increase of this ratio the degree of conversion of the starting components increases, but selectivity (for the desired product) is lowered. For this reason, from this standpoint a mixture of the stoichiometric composition is the most preferable. Extension of the contact time over 8 seconds is inexpedient, since yields of the desired products change in this case but insignificantly.

The catalyst can be used with or without a binder; as the latter, use can be made of an additive of $Al_2O_3$, $SiO_2$ or a mixture of both. The use of a binder makes it possible to obtain stronger catalysts of a different shape (granules, rings and the like).

The process of oxidation of benzene or derivatives thereof is an exothermal reaction. Hence, it is advisable to use an inert gas which lowers the thermal load on the catalyst. This makes it possible to avoid catalyst overheating and contributes to elevation of the reaction selectivity in respect of the desired products.

The process for preparing oxygen-containing benzene derivatives is simple and can be effected in the following manner.

The process for producing the catalyst is conventional and consists in the following (Ione K. G., Vostrikova L. A., Uspekhi Khimii, 1987, vol. LVI, iss. 3, pp. 393-427). A mixture consisting of a source of silicon, a source of iron and, when necessary, a source of $El^{n+}$, an alkali, organic surfactants and, in some cases, a crystallization seed, is homogenized and then placed into an autoclave, wherein under hydrothermal conditions it is kept for 1 to 30 days at a temperature within the range of from 80° C. to 200° C. On completion of crystallization, the residue is filtered off, washed with distilled water and dried. Prior to catalytic tests, the solid product is calcined at a temperature within the range of from 520° C. to 550° C. for the removal of organic inclusions and, if required, decationization is conducted using solutions of $NH_4OH + NH_4Cl$ or solutions of inorganic acids. In some cases a required element is introduced into the iron-silicate matrix using ion-exchange methods (Ione K. G. Polyfunctional Catalysis on Zeolites. Novosibirsk, "Nauka" Publishers, 1982, pp. 97-137) or impregnation (Dzisko V. A. Foundations of Methods for Preparation of Catalysts. Novosibirsk, "Nauka" Publishers, 1983, pp. 148-161).

The catalyst is charged into a reactor with an inside diameter of 7 mm. The catalyst volume is 2 cm³, particle size is 0.5-1 mm. The catalyst is heated to the predetermined temperature, and the reaction mixture, benzene or a derivative thereof, nitrogen oxide and, when required, helium or any other inert gas, is introduced at an appropriate rate. After contact with the catalyst, the mixture is subjected to condensation. The desired products are isolated by conventional techniques such as by rectification.

The mixture composition before and after reaction is determined by way of a chromatographic analysis, and from the obtained data, the degree of conversion of benzene or of the derivative thereof is calculated by the formula:

$$X = (C_i - C_o)/C_i,$$

wherein:

X is degree of conversion of benzene or its derivative, %; $C_i$ is the benzene concentration (or concentration of its derivative) at the inlet of the reactor, mol. %;
$C_o$ is the concentration of benzene or its derivative at the outlet of the reactor, mol. %;
Selectivity with respect to the desired product is calculated by the formula:

$$S = C_p/(C_i - C_o),$$

wherein

S is the selectivity with respect to the desired product, %;
$C_i$ is the concentration of benzene or a derivative thereof at the inlet of the reactor, mol. %;
$C_o$ is the concentration of benzene or its derivative at the outlet of the reactor, mol. %;
$C_p$ is the concentration of the desired product of the reaction, mol. %.

Yields of the desired product are calculated by the formula:

$$Y = X \cdot S/100,$$

wherein:

X—conversion of benzene or its derivative, %
S—selectivity with respect to the desired product, %.

Given hereinafter are characteristics averaged for three hours of operation of the catalyst.

After the stage of oxidation of benzene or a derivative thereof, the catalyst is regenerated with oxygen or air, or with nitrogen oxide at a temperature within the range of from 400° C. to 550° C. and again used for oxidation of benzene or its derivative. Properties of the catalyst in the reaction of oxidation remain unchanged after more than 20 cycles of its regeneration.

The process for preparing phenol or phenol derivatives, as compared to the known ones, ensures increased yields of the desired products, up to 37%, which is considerably higher than the corresponding parameter in the prior art process obtained under similar conditions (Suzuki, E., Nakeshiro K., Ono Y. Chemistry Letters, 1988, No. 6, pp. 953-956). The process features a simple procedure, is effected in a single stage and necessitates no use of aggressive reagents. Furthermore, the process according to the present invention makes it possible to obtain a whole number of oxygen-containing benzene derivatives such as phenol, benzoquinone, dihydric phenols, cresols, chlorophenols and the like.

For a better understanding of the present invention, some specific examples are given hereinbelow by way of illustration.

EXAMPLE 1

A synthetic zeolite of the composition $8.2 \cdot 10^{-3} \cdot Fe_2O_3 \cdot SiO_2$ with the structure ZSM-5 in the amount of 2 cm³ was charged into a reactor, heated to the temperature of 350° C. and a reaction mixture of the composition: 5 mol. % benzene, 20 mol. % nitrous oxide, the balance, helium, was fed thereinto at the rate of 1 cm³/sec. The reaction mixture composition was discontinuously (once every 15 minutes) analyzed by means of a chromatograph. Apart from phenol and carbon dioxide, no other carbon-containing compounds were detected in the reaction products. The process had the following parameters:

| | |
|---|---|
| conversion of benzene, X | 15.4% |
| selectivity for phenol, S | 99.0% |
| yield of phenol, Y | 15.3% |

EXAMPLES 2-15

Phenol was obtained as in Example 1, except that temperature was varied as was the time of contact of the reaction mixture with the catalyst, wherefor at the same space velocity (1 cm³/sec) the catalyst charge was changed from 2 to 8 cm³. The catalyst characteristics, its temperature, the time of contact of the reaction mixture with the catalyst and the test results are shown in Table 1 hereinbelow.

EXAMPLE 16

Phenol was prepared in a manner similar to that described in Example 1 hereinbefore, except that the reaction mixture had the following composition: 5 mol. % benzene, and 95 mol. % nitrous oxide.

The process parameters were as follows:

| | |
|---|---|
| conversion of benzene, X | 18.0% |
| selectivity for phenol, S | 83.5% |
| yield of phenol, Y | 15.0% |

TABLE 1

Effect of the Contact Time and Temperature on the Parameters of the Process of Oxidation of Benzene into Phenol on the Catalyst of the Composition $8.2 \cdot 10^{-3}$ $Fe_2O_3$ $SiO_2$ with the Structure ZSM-5 (Composition of the Starting Feed: Benzene-5 mol. %, Nitrogen Oxide-20 mol %).
Averaged Characteristics for 3 Hours' Operation

| Example No. | T, °C. | Conversion of $C_6H_6$ X, % | Selectivity for $C_6H_5OH$ S, % | Yield of $C_6H_5OH$ Y, % |
|---|---|---|---|---|
| Contact Time 1 sec. | | | | |
| 2 | 375 | 10.3 | 98.0 | 9.2 |
| Contact Time 2 sec. | | | | |
| 3 | 300 | 8.4 | 100.0 | 8.4 |
| 4 | 375 | 22.4 | 94.3 | 21.0 |
| 5 | 400 | 28.9 | 88.0 | 25.4 |
| 6 | 420 | 35.5 | 71.0 | 25.3 |
| Contact Time 4 sec. | | | | |
| 7 | 275 | 13.7 | 100.0 | 13.7 |
| 8 | 300 | 17.8 | 99.7 | 17.7 |
| 9 | 325 | 23.5 | 97.5 | 22.9 |
| 10 | 350 | 30.8 | 93.4 | 28.8 |
| 11 | 400 | 46.3 | 55.8 | 25.3 |

TABLE 1-continued

Effect of the Contact Time and Temperature on the Parameters of the Process of Oxidation of Benzene into Phenol on the Catalyst of the Composition $8.2 \cdot 10^{-3} Fe_2O_3 \cdot SiO_2$ with the Structure ZSM-5 (Composition of the Starting Feed: Benzene-5 mol. %, Nitrogen Oxide-20 mol %). Averaged Characteristics for 3 Hours' Operation

| Example No. | T, °C. | Conversion of $C_6H_6$ X, % | Selectivity for $C_6H_5OH$ S, % | Yield of $C_6H_5OH$ Y, % |
|---|---|---|---|---|
| | | Contact Time 8 sec. | | |
| 12 | 275 | 14.2 | 100.0 | 14.2 |
| 13 | 300 | 22.1 | 98.0 | 21.7 |
| 14 | 325 | 31.4 | 96.1 | 30.2 |
| 15 | 350 | 39.0 | 90.4 | 35.3 |

EXAMPLES 17-82

Phenol was prepared as in Example 1 hereinbefore, except that varied were chemical compositions of the catalysts, their structure and the reaction temperature. Characteristics of the catalysts, temperature of the reaction nd the results of tests are shown in Table 2 hereinbelow.

EXAMPLE 83

Phenol was produced in a manner similar to that described in Example 1 hereinbefore, except that use was made of a catalyst having the composition of $8.4 \cdot 10^{-3} \cdot Fe_2O_3 \cdot SiO_2$ containing, as the binder, 20% by mass of $Al_2O_3$.

The process parameters were as follows:

| | |
|---|---|
| conversion of benzene, X | 32.0% |
| selectivity for phenol, S | 97.2% |
| yield of phenol, Y | 31.2%. |

EXAMPLE 84

Phenol was obtained as described in Example 1 hereinbefore, except that use was made of a catalyst of the composition of $8.4 \cdot 10^{-3} \cdot Fe_2O_3 \cdot SiO_2$ containing, as the binder, 25% by mass of $SiO_2$.

The process had the following parameters:

| | |
|---|---|
| conversion of benzene, X | 27.7% |
| selectivity for phenol, S | 96.8% |
| yield of phenol, Y | 26.8%. |

EXAMPLE 84

Phenol was prepared in a manner similar to that described in Example 1 hereinbefore, except that use was made of a catalyst of the composition of $8.4 \cdot 10^{-3} \cdot Fe_2O_3 \cdot SiO_2$ containing, as the binder, 1% by mass of $SiO_2$.

The process had the following parameters:

| | |
|---|---|
| conversion of benzene, X | 29.2% |
| selectivity for phenol, S | 97.0% |
| yield of phenol, Y | 28.3% |

TABLE 2

| Example No. | Catalyst composition molar ratio | Structure | T, °C. | Averaged parameters for 3 hours of operation | | |
|---|---|---|---|---|---|---|
| | | | | X, % | S, % | Y, % |
| 17 | $2.0 \cdot 10^{-4} \cdot Fe_2O_3 \cdot SiO_2$ | ZSM-5 | 500 | 2.0 | 100.0 | 2.0 |
| 18 | $2.0 \cdot 10^{-3} \cdot Fe_2O_3 \cdot SiO_2$ | ZSM-5 | 425 | 25.5 | 94.0 | 24.0 |
| 19 | $4.9 \cdot 10^{-3} \cdot Fe_2O_3 \cdot SiO_2$ | ZSM-5 | 350 | 22.6 | 82.6 | 18.7 |
| 20 | $9.4 \cdot 10^{-3} \cdot Fe_2O_3 \cdot SiO_2$ | ZSM-5 | 400 | 29.5 | 81.5 | 24.0 |
| 21 | $2.0 \cdot 10^{-2} \cdot Fe_2O_3 \cdot SiO_2$ | ZSM-5 | 330 | 28.6 | 91.0 | 26.0 |
| 22 | $2.0 \cdot 10^{-2} \cdot Fe_2O_3 \cdot SiO_2$ | ZSM-5 | 350 | 47.0 | 78.7 | 37.6 |
| 23 | $1.2 \cdot 10^{-3} \cdot Al_2O_3 \cdot 3 \cdot 10^{-5} \cdot Fe_2O_3 \cdot SiO_2$ | ZSM-5 | 500 | 2.0 | 100.0 | 2.0 |
| 24 | $3.8 \cdot 10^{-3} \cdot Al_2O_3 \cdot 3 \cdot 10^{-4} \cdot Fe_2O_3 \cdot SiO_2$ | ZSM-5 | 450 | 5.5 | 100.0 | 5.5 |
| 25 | $3.8 \cdot 10^{-3} \cdot Al_2O_3 \cdot 3 \cdot 10^{-4} \cdot Fe_2O_3 \cdot SiO_2$ | ZSM-5 | 500 | 7.9 | 82.0 | 6.3 |
| 26 | $2.5 \cdot 10^{-2} \cdot Al_2O_3 \cdot 1.6 \cdot 10^{-3} \cdot Fe_2O_3 \cdot SiO_2$ | ZSM-5 | 330 | 6.3 | 100.0 | 6.3 |
| 27 | $2.5 \cdot 10^{-2} \cdot Al_2O_3 \cdot 1.6 \cdot 10^{-3} \cdot Fe_2O_3 \cdot SiO_2$ | ZSM-5 | 350 | 9.2 | 97.0 | 9.0 |
| 28 | $2.5 \cdot 10^{-2} \cdot Al_2O_3 \cdot 1.6 \cdot 10^{-3} \cdot Fe_2O_3 \cdot SiO_2$ | ZSM-5 | 375 | 14.5 | 72.0 | 10.5 |
| 29 | $2.5 \cdot 10^{-2} \cdot Al_2O_3 \cdot 1.6 \cdot 10^{-3} \cdot Fe_2O_3 \cdot SiO_2$ | ZSM-5 | 400 | 24.7 | 37.0 | 9.2 |
| 30 | $10^{-2} \cdot Al_2O_3 \cdot 2.8 \cdot 10^{-3} \cdot Fe_2O_3 \cdot SiO_2$ | ZSM-5 | 330 | 10.0 | 97.0 | 9.7 |
| 31 | $10^{-2} \cdot Al_2O_3 \cdot 2.8 \cdot 10^{-3} \cdot Fe_2O_3 \cdot SiO_2$ | ZSM-5 | 350 | 13.0 | 92.0 | 11.9 |
| 32 | $10^{-2} \cdot Al_2O_3 \cdot 2.8 \cdot 10^{-3} \cdot Fe_2O_3 \cdot SiO_2$ | ZSM-5 | 375 | 17.0 | 70.5 | 12.0 |
| 33 | $10^{-2} \cdot Al_2O_3 \cdot 2.8 \cdot 10^{-3} \cdot Fe_2O_3 \cdot SiO_2$ | ZSM-5 | 400 | 32.0 | 33.0 | 10.5 |
| 34 | $10^{-2} \cdot Al_2O_3 \cdot 1.9 \cdot 10^{-3} \cdot Fe_2O_3 \cdot SiO_2$ | ZSM-5 | 375 | 28.0 | 50.0 | 14.0 |
| 35 | $10^{-2} \cdot Al_2O_3 \cdot 1.2 \cdot 10^{-3} \cdot Fe_2O_3 \cdot SiO_2$ | ZSM-5 | 300 | 8.4 | 100.0 | 8.4 |
| 36 | $10^{-2} \cdot Al_2O_3 \cdot 1.2 \cdot 10^{-3} \cdot Fe_2O_3 \cdot SiO_2$ | ZSM-5 | 325 | 15.0 | 100.0 | 15.0 |
| 37 | $10^{-2} \cdot Al_2O_3 \cdot 1.2 \cdot 10^{-3} \cdot Fe_2O_3 \cdot SiO_2$ | ZSM-5 | 350 | 18.0 | 99.0 | 17.3 |
| 38 | $10^{-2} \cdot Al_2O_3 \cdot 1.2 \cdot 10^{-3} \cdot Fe_2O_3 \cdot SiO_2$ | ZSM-5 | 375 | 20.9 | 96.0 | 20.0 |

TABLE 2-continued

| Example No. | Catalyst composition molar ratio | Structure | T, °C. | X, % | S, % | Y, % |
|---|---|---|---|---|---|---|
| 39 | $10^{-2}.Al_2O_3.1.2 \cdot 10^{-3}.Fe_2O_3.SiO_2$ | ZSM-5 | 500 | 31.0 | 10.0 | 3.1 |
| 40 | $10^{-2}.Al_2O_3.2.8 \cdot 10^{-4}.Fe_2O_3.SiO_2$ | ZSM-5 | 350 | 4.9 | 100.0 | 4.9 |
| 41 | $10^{-2}.Al_2O_3.2.8 \cdot 10^{-4}.Fe_2O_3.SiO_2$ | ZSM-5 | 330 | 11.0 | 100.0 | 11.0 |
| 42 | $10^{-2}.Al_2O_3.2.8 \cdot 10^{-4}.Fe_2O_3.SiO_2$ | ZSM-5 | 400 | 20.4 | 98.0 | 20.0 |
| 43 | $10^{-2}.Al_2O_3.2.8 \cdot 10^{-4}.Fe_2O_3.SiO_2$ | ZSM-5 | 425 | 20.7 | 94.0 | 19.5 |
| 44 | $10^{-2}.Al_2O_3.1.5 \cdot 10^{-5}.Fe_2O_3.SiO_2$ | ZSM-5 | 350 | 2.2 | 100.0 | 2.2 |
| 45 | $10^{-2}.Al_2O_3.1.5 \cdot 10^{-5}.Fe_2O_3.SiO_2$ | ZSM-5 | 400 | 9.7 | 100.0 | 9.7 |
| 46 | $10^{-2}.Al_2O_3.1.5 \cdot 10^{-5}.Fe_2O_3.SiO_2$ | ZSM-5 | 450 | 11.6 | 100.0 | 11.6 |
| 47 | $1.1 \cdot 10^{-2}.TiO_2.5.8 \cdot 10^{-4}.Fe_2O_3.7.5 \cdot 10^{-3}.Al_2O_3.SiO_2$ | ZSM-5 | 450 | 7.6 | 96.0 | 7.3 |
| 48 | $2.0 \cdot 10^{-2}.TiO_2.2.0 \cdot 10^{-3}.Fe_2O_3.SiO_2$ | ZSM-5 | 375 | 16.0 | 98.0 | 15.7 |
| 49 | $1.1 \cdot 10^{-2}.Na_2O.8.4 \cdot 10^{-3}.Fe_2O_3.SiO_2$ | ZSM-5 | 400 | 11.8 | 95.0 | 11.2 |
| 50 | $1.1 \cdot 10^{-2}.Na_2O.10^{-2}.Al_2O_3.3.0 \cdot 10^{-4}.Fe_2O_3.SiO_2$ | ZSM-5 | 350 | 4.3 | 100.0 | 4.3 |
| 51 | $1.1 \cdot 10^{-2}.Na_2O.10^{-2}.Al_2O_3.3.0 \cdot 10^{-4}.Fe_2O_3.SiO_2$ | ZSM-5 | 400 | 12.6 | 100.0 | 12.6 |
| 52 | $7.9 \cdot 10^{-3}.Na_2O.10^{-2}.Al_2O_3.3.0 \cdot 10^{-4}.Fe_2O_3.SiO_2$ | ZSM-5 | 350 | 7.4 | 100.0 | 7.4 |
| 53 | $7.9 \cdot 10^{-3}.Na_2O.10^{-2}.Al_2O_3.3.0 \cdot 10^{-4}.Fe_2O_3.SiO_2$ | ZSM-5 | 400 | 19.9 | 98.0 | 19.5 |
| 54 | $6.0 \cdot 10^{-4}.Na_2O.10^{-2}.Al_2O_3.3.0 \cdot 10^{-4}.Fe_2O_3.SiO_2$ | ZSM-5 | 350 | 15.4 | 100.0 | 15.4 |
| 55 | $6.0 \cdot 10^{-4}.Na_2O.10^{-2}.Al_2O_3.3.0 \cdot 10^{-4}.Fe_2O_3.SiO_2$ | ZSM-5 | 400 | 23.4 | 97.6 | 22.9 |
| 56 | $10^{-2}.ZnO.10^{-2}.Al_2O_3.10^{-3}.Fe_2O_3.SiO_2$ | ZSM-5 | 400 | 10.0 | 80.0 | 8.0 |
| 57 | $1.8 \cdot 10^{-4}.Co_2O_3.10^{-2}.Al_2O_3.3.4 \cdot 10^{-5}.Fe_2O_3.SiO_2$ | ZSM-5 | 375 | 10.1 | 100.0 | 10.1 |
| 58 | $1.8 \cdot 10^{-4}.Co_2O_3.10^{-2}.Al_2O_3.3.4 \cdot 10^{-5}.Fe_2O_3.SiO_2$ | ZSM-5 | 400 | 11.7 | 100.0 | 11.7 |
| 59 | $1.8 \cdot 10^{-4}.Co_2O_3.10^{-2}.Al_2O_3.3.4 \cdot 10^{-5}.Fe_2O_3.SiO_2$ | ZSM-5 | 425 | 15.4 | 100.0 | 15.4 |
| 60 | $1.8 \cdot 10^{-4}.Co_2O_3.10^{-2}.Al_2O_3.3.4 \cdot 10^{-5}.Fe_2O_3.SiO_2$ | ZSM-5 | 450 | 18.7 | 99.4 | 18.6 |
| 61 | $4.4 \cdot 10^{-4}.Co_2O_3.10^{-2}.Al_2O_3.1.5 \cdot 10^{-5}.Fe_2O_3.SiO_2$ | ZSM-5 | 450 | 9.4 | 100.0 | 9.4 |
| 62 | $1.2 \cdot 10^{-4}.V_2O_3.7.6 \cdot 10^{-3}.Al_2O_3.4.2 \cdot 10^{-5}.Fe_2O_3.SiO_2$ | ZSM-5 | 400 | 8.4 | 100.0 | 8.4 |
| 63 | $1.2 \cdot 10^{-4}.V_2O_3.7.6 \cdot 10^{-3}.Al_2O_3.4.2 \cdot 10^{-5}.Fe_2O_3.SiO_2$ | ZSM-5 | 450 | 9.8 | 99.8 | 9.8 |
| 64 | $10^{-4}.Cr_2O_3.10^{-2}.Al_2O_3.2.0 \cdot 10^{-5}.Fe_2O_3.SiO_2$ | ZSM-5 | 450 | 9.0 | 99.0 | 8.9 |
| 65 | $3.0 \cdot 10^{-4}.Mn_2O_3.10^{-2}.Al_2O_3.6.0 \cdot 10^{-5}.Fe_2O_3.SiO_2$ | ZSM-5 | 425 | 8.5 | 98.3 | 8.3 |
| 66 | $4.0 \cdot 10^{-4}.NiO.10^{-2}.Al_2O_3.2.7 \cdot 10^{-3}.Fe_2O_3.SiO_2$ | ZSM-5 | 425 | 10.0 | 99.0 | 9.7 |
| 67 | $7.1 \cdot 10^{-4}.Mo_2O_3.10^{-2}.Al_2O_3.3.0 \cdot 10^{-3}.Fe_2O_3.SiO_2$ | ZSM-5 | 425 | 12.0 | 99.0 | 11.9 |
| 68 | $7.1 \cdot 10^{-3}.B_2O_3.10^{-3}.Fe_2O_3.SiO_2$ | ZSM-5 | 350 | 14.8 | 99.0 | 14.8 |

TABLE 2-continued

| Example No. | Catalyst composition molar ratio | Structure | T, °C. | X, % | S, % | Y, % |
|---|---|---|---|---|---|---|
| 69 | $5.0 \cdot 10^{-4}.Na_2O.$<br>$9.0 \cdot 10^{-3}.Al_2O_3.$<br>$4.0 \cdot 10^{-4}.Fe_2O_3.SiO_2$ | ZSM-5 | 350 | 6.0 | 100.0 | 6.0 |
| 70 | $5.0 \cdot 10^{-4}.Na_2O.$<br>$9.0 \cdot 10^{-3}.Al_2O_3.$<br>$4.0 \cdot 10^{-4}.Fe_2O_3.SiO_2$ | ZSM-5 | 400 | 10.0 | 100.0 | 10.0 |
| 71 | $1.1 \cdot 10^{-2}.CaO.$<br>$4.2 \cdot 10^{-3}.MgO.10^{-2}.Al_2O_3.$<br>$3.4 \cdot 10^{-3}.Fe_2O_3.SiO_2$ | ZSM-11 | 350 | 4.1 | 100.0 | 4.0 |
| 72 | $1.1 \cdot 10^{-2}.CaO.$<br>$4.2 \cdot 10^{-3}.MgO.10^{-2}.Al_2O_3.$<br>$3.4 \cdot 10^{-3}.Fe_2O_3.SiO_2$ | ZSM-11 | 400 | 7.7 | 100.0 | 7.7 |
| 73 | $1.1 \cdot 10^{-2}.CaO.$<br>$4.2 \cdot 10^{-3}.MgO.10^{-2}.Al_2O_3.$<br>$3.4 \cdot 10^{-3}.Fe_2O_3.SiO_2$ | ZSM-11 | 425 | 9.9 | 98.0 | 9.4 |
| 74 | $5.0 \cdot 10^{-3}.Al_2O_3.$<br>$3.5 \cdot 10^{-4}.Fe_2O_3.SiO_2$ | ZSM-12 | 350 | 8.0 | 100.0 | 8.0 |
| 75 | $5.0 \cdot 10^{-3}.Al_2O_3.$<br>$3.5 \cdot 10^{-4}.Fe_2O_3.SiO_2$ | ZSM-12 | 400 | 15.3 | 97.0 | 14.8 |
| 76 | $6.5 \cdot 10^{-2}.Al_2O_3.$<br>$5.4 \cdot 10^{-4}.Fe_2O_3.SiO_2$ | mordenite | 350 | 7.2 | 100.0 | 7.2 |
| 77 | $6.5 \cdot 10^{-2}.Al_2O_3.$<br>$5.4 \cdot 10^{-4}.Fe_2O_3.SiO_2$ | mordenite | 400 | 14.2 | 100.0 | 14.2 |
| 78 | $6.5 \cdot 10^{-2}.Al_2O_3.$<br>$5.4 \cdot 10^{-4}.Fe_2O_3.SiO_2$ | mordenite | 425 | 22.3 | 99.0 | 22.1 |
| 79 | $6.5 \cdot 10^{-2}.Al_2O_3.$<br>$5.4 \cdot 10^{-4}.Fe_2O_3.SiO_2$ | mordenite | 450 | 32.4 | 86.4 | 26.2 |
| 80 | $5.0 \cdot 10^{-5}.Na_2O.$<br>$1.2 \cdot 10^{-2}.Al_2O_3.$<br>$1.1 \cdot 10^{-3}.Fe_2O_3.SiO_2$ | ZSM-23 | 350 | 14.5 | 100.0 | 14.5 |
| 81 | $3.1 \cdot 10^{-4}.Na_2O.$<br>$6.0 \cdot 10^{-2}.Al_2O_3.$<br>$1.2 \cdot 10^{-3}.Fe_2O_3.SiO_2$ | BETA | 350 | 9.8 | 99.0 | 9.7 |
| 82 | $6.1 \cdot 10^{-4}.Na_2O.$<br>$10^{-2}.Al_2O_3.1.4 \cdot$<br>$10^{-3}.Fe_2O_3.SiO_2$ | EU-1 | 350 | 15.0 | 98.0 | 14.5 |

EXAMPLE 86

Phenol was prepared as in Example 1 hereinbefore, except that use was made of a catalyst having the composition of $8.4 \cdot 10^{-3}.Fe_2O_3.SiO_2$ containing, as the binder, 29% by mass of $Al_2O_3$ and 70% by mass of $SiO_2$, and the process was conducted at the temperature of 450° C. The process had the following parameters:

| | |
|---|---|
| conversion of benzene, X | 9.5% |
| selectivity for phenol, S | 98.0% |
| yield of phenol, Y | 9.3% |

EXAMPLE 87

A synthetic zeolite of the composition of $1.10 \cdot 10^{-4}.Na_2O. 1.10^{-4}. Al_2O_3.8.4 \cdot 10^{-3}.Fe_2O_3.SiO_2$ with the structure of ZSM-5 in the amount of 2 cm³ was charged into a reactor, heated to the temperature of 350° C. and a reaction mixture of the composition: 5 mol. % benzene, 20 mol. % nitrous oxide, the balance, helium, was fed thereinto at the rate of 1 cm³/sec. After the reactor the mixture composition was discontinuously (once every 15 minutes) analyzed by means of a chromatograph. Along with phenol there were formed: benzoquinone, diphenylmethane, cresol and dibenzofuran. The process parameters were the following:

| | |
|---|---|
| conversion of benzene | 47.6% |
| selectivity for phenol | 78.7% |
| selectivity for benzoquinone | 7.2% |
| selectivity for diphenylmethane | 8.0% |
| selectivity for dibenzofuran | 0.2%. |

The total yield of the products of partial oxidation was equal to 45.2%.

EXAMPLE 88

A zeolite of the composition of $5.10^{-3}.P_2O_5.4.10^{-4}. Al_2O_310^{-2}.Fe_2O_3.SiO_2$ with the structure of ZSM-5 was charged into a reactor in the amount of 2 cm³, heated to the temperature of 350° C. and a reaction mixture of the composition: 2 mol. % phenol, 20 mol. % nitrous oxide, the balance, helium, was fed into the reactor at the rate of 1 cm³/sec. The mixture composition after the reactor was analyzed by means of a chromatograph. The main products of the reaction were pyrocatechol and benzoquinone. The process had the following parameters:

| | |
|---|---|
| conversion of phenol | 8.0% |
| selectivity for pyrocatechol | 77.8% |
| selectivity for benzoquinone | 16.4% |
| total yield of the products of partial oxidation | 7.5% |

EXAMPLE 89

Pyrocatechol and benzoquinone were prepared in a manner similar to that described in Example 88, except that the charge of the catalyst was increased to 4 cm$^3$. The process parameters were the following:

| | |
|---|---|
| conversion of phenol | 11.5% |
| selectivity for pyrocatechol | 76.0% |
| selectivity for benzoquinone | 16.0% |
| total yield of the products of partial oxidation | 10.7% |

EXAMPLE 90

A zeolite of the composition: $10^{-2}.Al_2O_3.2.8.10^{-4}.Fe_2O_3.SiO_2$ with the structure ZSM-5 in the amount of 4 cm$^3$ was charged into a reactor, heated to the temperature of 375° C. and a reaction mixture: 2 mol. % phenol, 20 mol. % nitrous oxide, the balance, helium, was fed thereinto at the rate of 1 cm$^3$/sec. The mixture composition after the reactor was discontinuously (once every 15 minutes) analyzed by means of a chromatograph. The main products of the reaction were pyrocatechol and hydroquinone. The process parameters averaged for 3 hours of operation were the following:

| | |
|---|---|
| conversion of phenol | 15.1% |
| selectivity for hydroquinone | 39.8% |
| selectivity for pyrocatechol | 22.6% |
| total yield of the products of partial oxidation | 9.4% |

EXAMPLE 91

A zeolite of the composition of $8.2.10^{-3}.Fe_2O_3.SiO_2$ with a structure of the ZSM-5 type was charged into a reactor in the amount of 2 cm$^3$, heated to the temperature of 350° C. and a reaction mixture of the composition: 5 mol. % chlorobenzene, 20 mol. % nitrous oxide, the balance, helium, was fed thereinto at the rate of 1 cm$^3$/sec. The mixture composition after the reactor was discontinuously (once every 15 minutes) analyzed by means of a chromatograph. The main products of the reaction were chlorophenols. The process parameters averaged for three hours of operation were the following:

| | |
|---|---|
| conversion of chlorobenzene | 17.0% |
| selectivity for para-chlorphenol | 39.0% |
| selectivity for ortho-chlorophenol | 60.0% |
| total yield of chlorophenol | 16.8% |

EXAMPLE 92

A zeolite of the composition of $8.4.10^{-3}.Fe_2O_3.SiO_2$ with a structure of the ZSM-5 type was charged into a reactor in the amount of 2 cm$^3$ and a reaction mixture of the composition: 5 mol. % toluene, 20 mol. % nitrogen oxide, the balance, helium, was fed into the reactor at the rate of 1 cm$^3$/sec. The mixture composition after the reactor was analyzed by means of a chromatograph. The main products of the reaction of oxidation were cresols (nearly equal amounts of ortho-, para- and meta-isomers) and diphenylethane (product of oxidizing dimerization of toluene). The process parameters were the following:

| | |
|---|---|
| conversion of toluene | 48.1% |
| total selectivity for cresols | 20.3% |
| selectivity for phenol | 1.8% |
| yield of oxygen-containing benzene derivatives | 10.6%. |

We claim:

1. A process for preparing phenol or derivatives thereof comprising oxidation of the aromatic nucleus of benzene or derivatives thereof with nitrous oxide at a temperature within the range of 275° C. to 450° C., in the presence of a zeolite catalyst of the composition: $y.El_2O_n.x.Fe_2O_3.SiO_2$, wherein $y=0-6.5$. $10^{-2}$, $x=1.5.10^{-5}-2.10^{-2}$, El at least one element of Periods 2, 3, 4 and 5 of the periodic system; n is valence of the element El and at a time of contact of the reaction mixture with the catalyst of not more than 8 seconds.

2. A process according to claim 1 wherein the zeolite catalyst has a structure analogous to ZSM-5, ZSM-11, ZSM-12, mordenite, BETA and/or EU.

3. A process according to claim 1 wherein phenol is produced from benzene.

4. A process according to claim 1 wherein phenol and benzoquinone are produced from benzene.

5. A process according to claim 1 wherein dihydric phenols are produced from phenol.

6. A process according to claim 1 wherein dihydric phenols and benzoquinone are produced from phenol.

7. A process according to claim 1 wherein halogen-containing phenols are produced from halogen-containing benzene.

8. A process according to claim 1 wherein cresols are produced from toluene.

9. A process according to claim 1 wherein said catalyst is used in combination with a binder employed in an amount of from 1.0% to 99.0% by mass.

10. A process according to claim 9, wherein the binder is alumina and/or silica.

11. A process according to claim 1 wherein the process is conducted in the presence of an inert gas.

* * * * *